(12) United States Patent
DeBellis et al.

(10) Patent No.: US 7,312,337 B2
(45) Date of Patent: Dec. 25, 2007

(54) OXADIAZOLES AND THEIR MANUFACTURE

(75) Inventors: Francesco DeBellis, Rochester, NY (US); Chang-Kyu Kim, deceased, late of Pittsford, NY (US); by Alice J. Kim, legal representative, New York, NY (US)

(73) Assignee: Eastman Kodak Company, Rochester, NY (US)

( * ) Notice: Subject to any disclaimer, the term of this patent is extended or adjusted under 35 U.S.C. 154(b) by 534 days.

(21) Appl. No.: 10/955,347

(22) Filed: Sep. 30, 2004

(65) Prior Publication Data

US 2006/0069262 A1    Mar. 30, 2006

(51) Int. Cl.
*C07D 271/06*   (2006.01)
(52) U.S. Cl. ...................... 548/131; 548/125
(58) Field of Classification Search .............. 548/125, 548/131
See application file for complete search history.

(56) References Cited

U.S. PATENT DOCUMENTS 3,907,809 A * 9/1975 Von Esch et al. ........... 546/148
4,007,185 A * 2/1977 Von Esch et al. ........... 544/333
4,558,058 A * 12/1985 Schonafinger et al. ...... 514/342

OTHER PUBLICATIONS

Kuebel et al (1982): STN International HCAPLUS database, Columbus (Ohio), accession No. 1982:69205.*
Merckx, Raymond, 1,2,4-Oxadiazole derivatives, Bulletin des Societes Chimiqus Belges (1949), pp. 58-65 with abstract.
Harry L. Yale, et al., "3,5-Disubstituted-1,2,4-oxadiazoles and 4,5-Dihydro-3,5-disubstituted-1,2,4-oxadiazoles", J. Heterocyclic Chem., vol. 15, 1978, pp. 1373-1378.

* cited by examiner

*Primary Examiner*—Golam M. M. Shameem
(74) *Attorney, Agent, or Firm*—Arthur E. Klueger

(57) ABSTRACT

An oxadiazole compound and process of making same, is represented by Formula I:

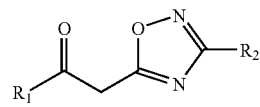

Formula I wherein $R_1$ represents a substituted or unsubstituted straight, branched, or cyclo-alkyl group having at least two carbon atoms, and $R_2$ represents an alkyl, aryl, or heteroaryl group.

19 Claims, No Drawings

OXADIAZOLES AND THEIR MANUFACTURE

CROSS REFERENCE TO RELATED APPLICATION

This application is being cofiled with an application Ser. No. 10/954,875 entitled METHOD FOR PREPARATION OF N-PYRAZOLYLAMIDOXIMES.

FIELD OF THE INVENTION

This invention relates to 5-(β-ketoalkyl)-3-substituted-1, 2,4-oxadiazoles, useful intermediates for preparation of 1H-pyrazolo[1,5-b]-1,2,4-triazole couplers in color photography.

BACKGROUND OF THE INVENTION

A new class of magenta-dye forming couplers used lately in color photography is 1H-pyrazolo[1,5-b]-1,2,4-triazole couplers. Image dyes formed from these couplers have an excellent light fastness. Examples are couplers disclosed in U.S. Pat. Nos. 4,540,654; 4,621,046; 4,882,266; 5,262,542; 5,378,587; 5,451,501; JP 60-197688; and JP 03-184980. The couplers have a unique 5/5 heterocyclic ring system. It has been solely synthesized solely from a 3-ketopropionitrile (1) as shown in the following scheme:

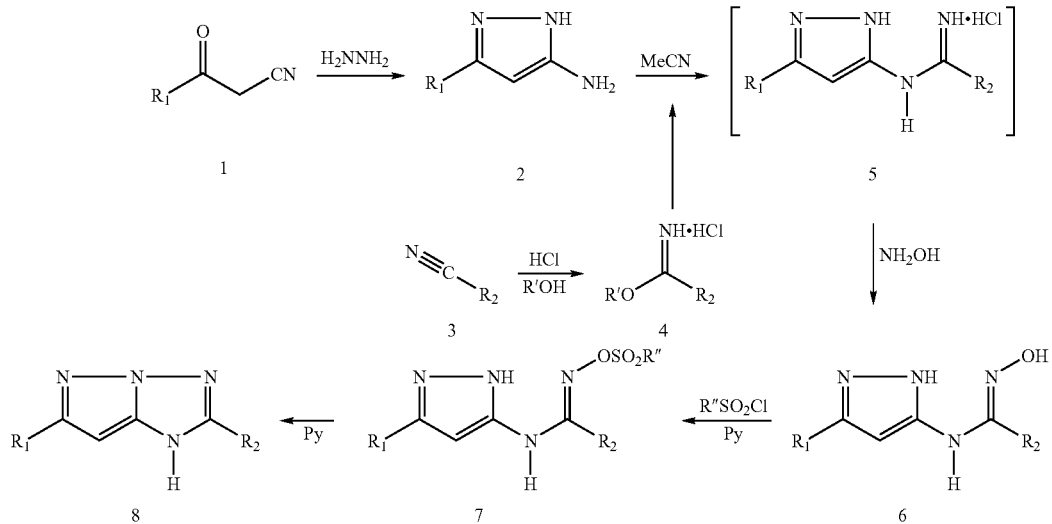

Reaction of a 3-ketoprionitrile (1) with hydrazine gives a 3-aminopyrazole (2). A 3-aminopyrazole )(2) is then reacted with an alkyl or aryl imidate ester hydrochloride (4) to give a N-pyrazolylamidine (5). An imidate ester hydrochloride (4) can be prepared by addition of an alcohol (R'OH) and hydrochloride to an alkyl or aryl nitrile (3). A N-pyrazolylamidine (5) can be converted to a N-pyrazolylamidoxime (6) by a reaction with hydroxylamine. O-Sulfonation of a N-pyrazolylamidoxime (6) with alkyl- or aryl-sulfonyl chloride (R"SO₂Cl) followed by ring closure gives a 1H-pyrazolo[1,5-b]-1,2,4-triazole (8). In this synthetic sequence 3-aminopyrazole (2) is a key intermediate for making a 1H-pyrazolo[1,5-b]-1,2,4-triazole coupler.

There are several disadvantages, however, in using 3-aminopyrazole (2) as a key intermediate for the preparation of 1H-pyrazolo[1,5-b]-1,2,4-triazole couplers.

(1) A 3-ketoprppionitrile (1) is not readily available. It is usually prepared from a commercially available precursor like a α-halo ketone by replacing halogen with cyanide. Such a replacement reaction with cyanide is difficult and has a lot of disadvantages in environment, safety, health, and cost issues.

(2) A 3-aminopyrazole (2) is known to be highly toxic. Its use as a raw material requires lots of upfront cost. It is another significant disadvantage in terms of environment, safety, health, and cost.

(3) Down-stream chemistry from 3-aminopyrazole (2) is inflexible. It has to be reacted with an imidate ester such as 4 in the next step. Most of imidate esters are so sensitive to water that they should be used in a strictly anhydrous medium. Any amount of water present causes formation of an amide that is not reactive at all in subsequent reactions. Reaction of a 3-aminopyrazole and an imidate ester gives either N-pyrazolyl-amidine or N-pyrazolyl-imidate dependent upon pH of medium. Either one of these intermediates can be transformed to N-pyazolylamidoxime in subsequent step. It is difficult, however, to get either one of the intermediates cleanly, so that it is used without isolation in the next step. The next step reaction requires free hydroxylamine that is liberated from commercially available salt form. It often requires a strong organic base such as triethylamine, 1,5-diazabicyclo[4,3,0]non-5-ene, or 1,8-diazabicyclo[5,4,0]-undec-7-ene, which is costly and causes difficulties in waste disposal. It is a disadvantage in environment, flexibility, and cost issues.

(4) The overall process described above is so complicated and dependent upon dryness of the medium that it gives a highly variable result. It is a disadvantage in terms of consistency, yield, and cost.

It is therefore desirable to develop a simplified, environmentally favorable, less toxic, and less expensive intermediate for the preparation of 1H-pyrazolo[1,5-b]-1,2,4-triazole magenta dye-forming couplers.

SUMMARY OF THE INVENTION

The present invention provides 5-(β-ketoalkyl)-3-substituted-1,2,4-oxadiazoles of the general formula I:

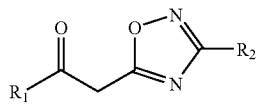

Formula I wherein
$R_1$ represents a straight chain or substituted alkyl group having at least two carbon atoms, and
$R_2$ represents an alkyl, aryl, or heteroaryl group.

The invention provides a simplified, environmentally favorable, less toxic, and less expensive intermediate for the preparation of 1H-pyrazolo[1,5-b]-1,2,4-triazole magenta dye-forming couplers.

DETAILED DESCRIPTION OF THE INVENTION

In the intermediate of Formula I, the group defined by $R_1$ is a straight chain or substituted alkyl having 2-40, particularly 2-30, carbon atoms.

Representative straight chain alkyl group is ethyl, propyl, butyl, pentyl, hexyl, heptyl, octyl, nonyl, decyl, undecyl, dodecyl, tridecyl, tetradecyl, pentadecyl, heptadecyl, octadecyl, or nonadecyl. Representative substituted alkyl groups are straight chain or branched alkyls having 1-30 carbon atoms and substituted with substituents that do not adversely affect the preparation and use of the intermediate. Examples of such substituents include an alkyl, aryl, heteroaryl, alkoxy, aryloxy, alkylthio, arylthio, alkoxycarbonyl, aryloxycarbonyl, acyl, acyloxy, carbonamido, carbamoyl, alkylsulfonyl, arylsulfonyl, sulfonamido, and sulfamoyl groups wherein the alkyl and aryl substituents, and the alkyl and aryl portions of the alkoxy, aryloxy, alkylthio, arylthio, alkoxycarbonyl, aryloxycarbonyl, acyl, acyloxy, carbohamido, carbamoyl, alkylsulfonyl, arylsulfonyl, sulfonamido, and sulfamnoyl substituents contain 1-30 carbon atoms and 6-30 carbon atoms, respectively, and can be further substituted with such substituents. Preferred $R_1$ groups include: a branched alkyl group such as isopropyl, sec-butyl, t-butyl, 1-ethylbutyl, t-pentyl, 2-ethylhexyl, or 2-hexyloctyl; a cyclic alkyl group such as cyclopropyl, cyclobutyl, cyclopentyl, cyclohexyl, 1-methylcyclopropyl, 1-methylcyclobutyl, 1-methylcyclopentyl, 1-methylcyclohexyl, or adamentyl; an arylalkyl group such as phenylmethyl, 4-chlorophenylmethyl, 4-methoxyphenylmethyl, 4-nitrophenylmethyl, 2-(4'-nitrophenyl)ethyl, or 3-(4'-nitrophenyl)propyl; an aryloxyalkyl group such as phenoxymethyl, 4-nitrophenoxymethyl, 2-(4-nitrophenoxy)ethyl, 3-(4-nitrophenoxy)propyl, 2,4-di-t-pentylphenoxymethyl, 1-(2,4-di-t-pentylphenoxy)propyl, 1-(2,4-di-t-pentylphenoxy)pentyl, 3-pentadecylphenoxymethyl, 1-(3-pentadecylphenoxy)propyl, 1-(4-butylsulfonylaminophenoxy)tridecyl, or 2-octylsulfonylaminophenoxymethyl; an alkylsulfonylalkyl such as 1-dodecylsulfonylpropyl, 3-dodecylsulfonylpentyl, 1-dodecylsulfonylpentyl, 1-dodecylsulfonyl-2-methypropyl, 1-tetradecylsulfonylpropyl, or1-hexadecylsulfonylpropyl; and an arylsufonylalkyl such as 1-(4-dodecyloxybenzenesulfonyl) propyl, or1-(4-hexadecyloxybenzensulfonyl) propyl.

In formula I, $R_2$ represents a substituent group in the art which, along with $R_1$, promotes solubility, diffusion resistance, dye hue, or dye stability of the dye formed upon reaction of the coupler with the oxidized color developing agent. Representative $R_2$ groups include alkyl, aryl, or heteroaryl groups having 1-40, particularly 1-30, carbon atoms, which may be unsubstituted or substituted with one or more substituents that do not adversely affect the preparation and use of the intermediate. Examples of such substituents include a halogen, nitro, cyano, carboxy, hydroxy, alkyl, aryl, heteroaryl, alkoxy, aryloxy, alkylthio, arylthio, alkyl amino, arylamino, alkoxycarbonyl, aryloxycarbonyl, acyl, acyloxy, acylamino, acylimino, carbonamido, carbamoyl, alkylsulfonyl, arylsulfonyl, sulfonamido, and sulfamoyl groups wherein the alkyl and aryl substituents, and the alkyl and aryl portions of the alkoxy, aryloxy, alkylthio, arylthio, alkylamino, arylamino, alkoxycarbonyl, aryloxycarbonyl, acyl, acyloxy, acylamino, acylimino, carbonamido, carbamoyl, alkylsulfonyl, arylsulfonyl, sulfonamido, and sulfamoyl substituents contain 1-30 carbon atoms and 6-30 carbon atoms, respectively, and can be further substituted with such substituents. Preferred $R_2$ groups include a substituted alkyl such as chloromethyl, 1-bromopropyl, 1-bromopentyl, 1-bromo-2-methylpropyl, 1-bromotridecyl, nitromethyl, cyanomethyl, 4-nitrophenylmethyl, 4-nitrophenylpropyl, 4-nitrophenoxymethyl, 1-(4-nitrophenoxy)propyl, 1-(4-nitrophenoxy)pentyl, 1-(4-nitrophenoxy)-2-methylpropyl, 1-(4-nitrophenoxy)-tridecyl, 1-(4-butylsulfonylaminophenoxy)tridecyl, 3-(4-nitrophenoxy)propyl, 2-phthalimidoethyl, 1-methyl-2-phthalimidoethyl, ethoxycarbonylmethyl, 1-dodecylsulfonylpropyl, 1-dodecylsulfonyl-2-methylpropyl, 1-tetradecylsulfonylpropyl, 1-hexadecylsulfonylpropyl, 1-(4-dodecyloxyphenylsulfonyl)propyl,1-(4-hexadecyloxyphenylsulfonyl)propyl, or 2-octylsulfonylaminophenoxymethyl; a substituted aryl group such as 2-nitrophenyl, 3-nitrophenyl, 4-nitrophenyl, 4-chloro-3-nitrophenyl, 2-butoxy-5-nitrophenyl, 4-ethoxycarbonylphenyl, 3-dodecyloxyphenyl, 4-dodecyloxyphenyl, 4-tetradecyloxyphenyl, 4-hexadecyloxyphenyl, or 2-(4-t-butylphenoxy)-5-nitrophenyl; and a substituted heteroaryl group such as 5-nitro-2-furyl, 2-butoxy-3-pyridyl, or 5-nitro-3-pyrazolyl.

The following are examples of oxadiazoles of the invention:

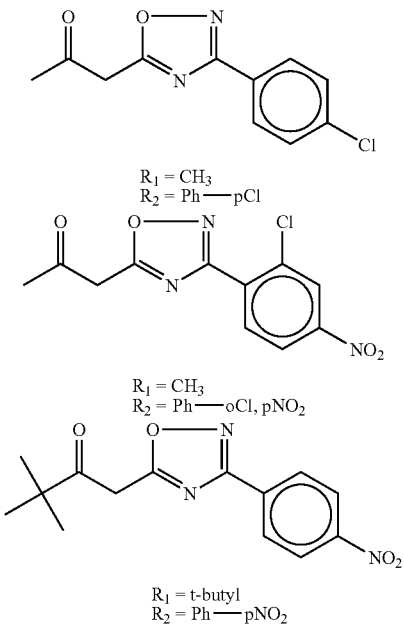

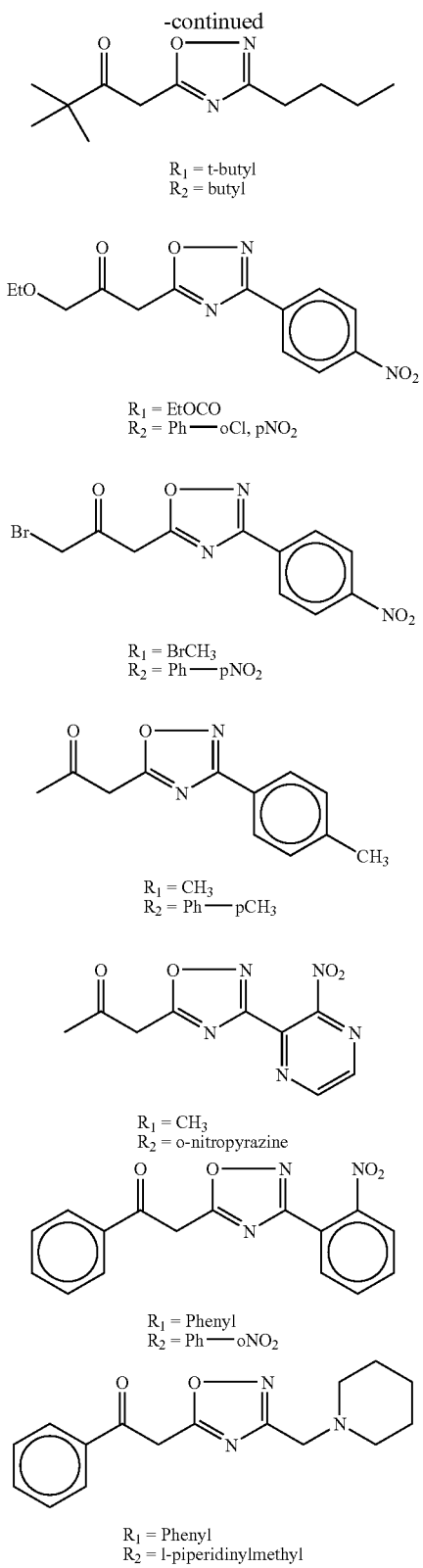

A process for preparing an intermediate of the invention comprises condensation of a β-keto-alkylester (10) with an amidoxime (9) and dehydrative cyclization as shown in the following scheme:

An amidoxime (2) is easily prepared from a nitrile (3). Addition of methanol to a nitrile (3) gives an imidate ester (4a) and subsequent reaction of the imidate ester with hydroxylamine gives an amidoxme (9). Some amidoximes (9) can be obtained directly from nitrile (3) by addition of hydroxylamine.

Unless otherwise specifically stated, use of the term "substituted" or "substituent" means any group or atom other than hydrogen. Unless otherwise provided, when a group, compound or formula containing a substitutable hydrogen is referred to, it is also intended to encompass not only the unsubstituted form, but also form further substituted with any substituent group or groups as herein mentioned, so long as the substituent does not destroy properties necessary for utility. Suitably, a substituent group may be halogen or may be bonded to the remainder of the molecule by an atom of carbon, silicon, oxygen, nitrogen, phosphorous, or sulfur. The substituent may be, for example, halogen, such as chloro, bromo or fluoro; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, cyclohexyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy) ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy)butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetraecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl) carbonylamino, p-dodecyl-phenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfonamoyl, N-ethylsulfamoyl, N,N-dipropylsulfamoyl, N-hexadecylsulfamoyl, N,N-diethylsulfamoyl; N-[3-(dodecyloxy) propyl] sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired desirable properties for a specific application and can include, for example, hydrophobic groups, solubilizing groups, blocking groups, and releasing or releasable groups. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected Down-stream chemistry from the intermediate of invention (Formula I) is simple and straightforward as shown in the following scheme:

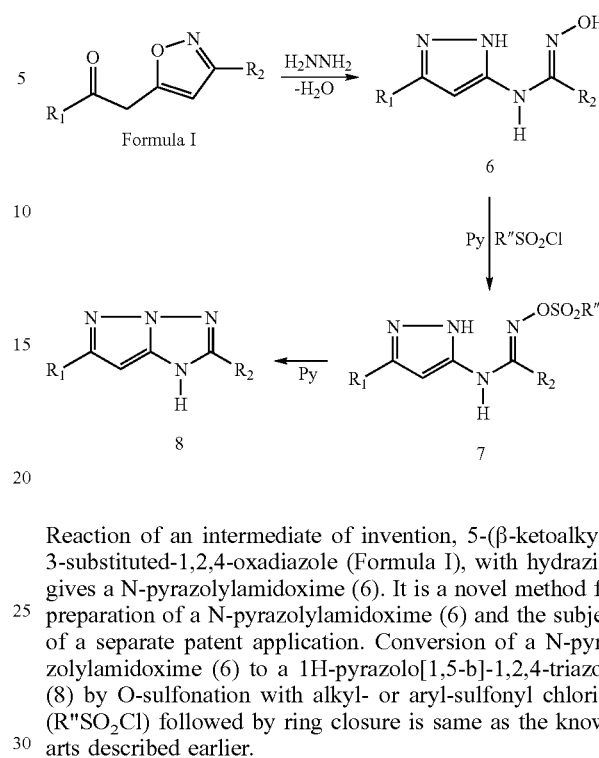

Reaction of an intermediate of invention, 5-(β-ketoalkyl)-3-substituted-1,2,4-oxadiazole (Formula I), with hydrazine gives a N-pyrazolylamidoxime (6). It is a novel method for preparation of a N-pyrazolylamidoxime (6) and the subject of a separate patent application. Conversion of a N-pyrazolylamidoxime (6) to a 1H-pyrazolo[1,5-b]-1,2,4-triazole (8) by O-sulfonation with alkyl- or aryl-sulfonyl chloride (R″SO$_2$Cl) followed by ring closure is same as the known arts described earlier.

Use of the intermediates of invention in making 1H-pyrazolo[1,5-b]-1,2,4-triazole magenta couplers has a number of advantages over the use of 3-ketopropionitriles (1) and 3-aminopyrazoles (2) in the prior arts.

(1) A β-ketoalkylester (10) is a readily available raw material. It is usually prepared from a commercially available methyl ketone (11) by condensation with dimethylcarbonate (12) as shown in the following:

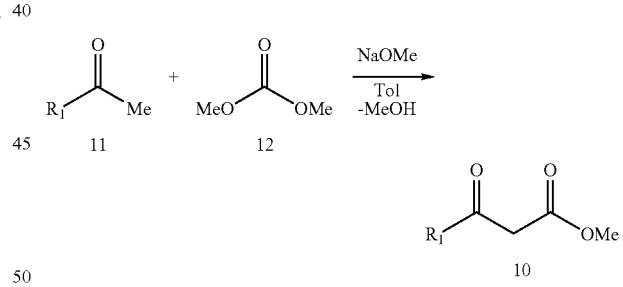

Such a condensation reaction is easy and does not impose any safety, toxicity, or environmental concern. Certain β-ketoalkylester is commercially available in a multi-ton quantity. For example, methyl 4,4-dimethyl-3-oxovalerate (10a; R$_1$=t-butyl) is a basic raw material for the preparation of many yellow dye-forming couplers, and available at a very low-cost. It is therefore a significant advantage in the issues of safety, health, environment, and cost.

(2) An amidoxime (9) is also a readily available intermediate. It is easily prepared from a corresponding nitrile by addition of methalol and subsequent reaction with hydroxylamine. A nitrile that contains an electron withdrawing substituent gives amidoxime directly by simple addition of hydroxylamine. Certain amidoximes such as 3-nitrobenzamidoxime (9a; R=3-nitrophenyl) and 4-nitrobenzamidoxime (9b; R=4-nitrophenyl) are commercially available and listed in a chemical regulatory clearance list. It is another significant advantage in health, environment, and cost issues.

(3) 5-(β-Ketoalkyl)-3-substituted-1,2,4-oxadiazoles (Formula I) have no amino group attached so that they may be less toxic than 3-aminopyrazoles in prior arts. Their uses as intermediates are environmentally more favorable and require less upfront cost for chemical regulatory clearance work. It is also advantage in the issues of health, environment, and cost.

(4) Down stream chemistry is simple and straightforward. A simple reaction of an oxadiazole (Formula I) with hydrazine gives-desired N-pyrazolylamidoxime (6) and only by-product is water. It is thus another advantage in terms of health, environment, and cost.

The invention provides a readily available, environmentally favorable, less toxic, and low-cost intermediate for the preparation of 1H-pyrazolo[1,5-b]-1,2,4-triazole magenta dye-forming couplers as shown in the background references.

EXAMPLE 1

5-(3,3-Dimethyl-2-oxobutyl)-3-(3-nitrophenyl)-1,2,4-oxadiazole [Formula I: $R_1$=t-butyl and $R_2$=3-nitrophenyl]

In a 500-ml flask, place 30.6 g (0.21 m) of 3-nitrobenzonitrile (3a; $R_2$=3-nitrophenyl) and 150 ml of methanol and stir to absolution. Add 48 g (0.22 m) of 25 wt. % sodium methoxide in methanol slowly and stir at room temperature for 1.5 hrs. Add 22.5 ml of acetic acid to make pH of reaction mixture around 6. Add 18.1 g (0.22 m) of sodium acetate and 22 g (0.32 m) of hydroxylamine hydrochloride. After a few minutes with stirring, the reaction mixture becomes thick yellow slurries. Stir the slurries at room temperature for 1 hr. Add 130 ml of water and stir for 15 min. Collect solid, wash with water and dry in air to give 30.5 g (80%) of 3-nitrobenzamidoxime (9a; R=3-nitrophenyl).

In a 250 ml flask, place 16 g (0.088 m) of 3-nitrobenzamidoxime (9a), 21.3 g (0.135 m) of methyl 4,4-dimethyl-3-oxovalerate (10a; $R_1$=t-butyl), and 120 ml of toluene. Heat and stir the reaction mixture under reflux with a Dean-Stark trap for 23 hrs. Distill off toluene under a reduced pressure at 50-60° C. to thick oil. Add 60 ml of heptane to the oil with stirring, cool and stir at 0-5° C. for 30 min. Collect solid, wash with heptane, and dry in air to give 22.9 g (90%) of 5-(3,3-dimethyl-2-oxobutyl)-3-(3-nitrophenyl)-1,2,4-oxadiazole [Formula I: $R_1$=t-butyl and $R_2$=3-nitrophenyl].

EXAMPLE 2

5-(3,3-Dimethyl-2-oxobutyl)-3-(4-nitrophenyl)-1,2,4-oxadiazole [Formula I: $R_1$=t-butyl and $R_2$=4-nitrophenyl]

Treating 29.6 g (0.2 m) of 4-nitrobenzonitrile (3b; $R_2$=4-nitrophenyl) in similar manner as Example 1 gives 23.0 g (90%) of 5-(3,3-dimethyl-2-oxobutyl)-3-(4-nitrophenyl)-1,2,4-oxadiazole [Formula I: $R_1$=t-butyl and $R_2$=4-nitrophenyl].

The patents and other publications cited herein are incorporated by reference in their entirety. The invention has been described in detail with particular reference to certain preferred embodiments thereof, but it will be understood that variations and modifications can be effected within the spirit and scope of the invention.

What is claimed is:

1. A process for preparing an oxadiazole compound of Formula I:

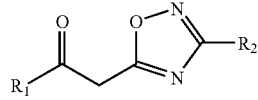

Formula I wherein
$R_1$ represents a substituted or unsubstituted straight, branched, or cyclo-alkyl group having at least two carbon atoms, and
$R_2$ represents an alkyl, aryl, or heteroaryl group; which comprises condensation of a β-keto-alkylester with an amidoxime and dehydrative cyclization.

2. The process of claim 1 wherein $R_1$ contains 2-30 carbon atoms.

3. The process of claim 2 wherein $R_1$ is an ethyl, propyl, butyl, pentyl, hexyl, heptyl, octyl, nonyl, decyl, undecyl, dodecyl, tridecyl, tetradecyl, pentadecyl, heptadecyl, octadecyl, or nonadecyl group.

4. The process of claim 2 wherein $R_1$ is a branched or cyclo-alkyl group.

5. The process of claim 4 wherein $R_1$ is a cyclopropyl, cyclobutyl, cyclopentyl, cyclohexyl, 1-methylcyclopropyl, 1-methylcyclobutyl, 1-methylcyclopentyl, 1-methylcyclohexyl, or adamentyl group.

6. The process of claim 2 wherein $R_1$ is a branched alkyl, cyclic alkyl, arylalkyl, aryloxyalkyl, alkylsulfonylalkyl, or arylsulfonyl-alkyl group.

7. The process of claim 6 wherein $R_1$ is an isopropyl, sec-butyl, t-butyl, 1-ethylbutyl, t-pentyl, 2-ethylhexyl, or 2-hexyloctyl group.

8. The process of claim 5 wherein $R_1$ is a phenylmethyl, 4-chlorophenylmethyl, 4-methoxyphenylmethyl, 4-nitrophenylmethyl, 2-(4'-nitro-phenyl)ethyl, or 3-(4'-nitrophenyl)propyl group.

9. The process of claim 5 wherein $R_1$ is a phenoxy-methyl, 4-nitrophenoxymethyl, 2-(4-nitrophenoxy)ethyl, 3-(4-nitrophenoxy)-propyl, 2,4-di-t-pentylphenoxymethyl, 1-(2,4-di-t-pentylphenoxy) propyl, 1-(2,4-di-t-pentylphenoxy)pentyl, 3-pentadecylphenoxymethyl, 1-(3-pentadecyl-phenoxy)propyl, 1-(4-butylsulfonylaminophenoxy)tridecyl, or 2-octyl-sulfonyl-aminophenoxymethyl group.

10. The process of claim 5 wherein $R_1$ is a 1-dodecyl-sulfonylpropyl, 3-dodecylsulfonylpropyl, 1-dodecylsulfonylpentyl, 1-dodecyl-sulfonyl-2-methylpropyl, 1-tertadecyl-sulfonylpropyl, or 1-hexadecylsulfonylpropyl group.

11. The process of claim 5 wherein $R_1$ is a 1-(4-dodecyloxybenzenesulfonyl)propyl, or a 1-(4-hexadecyloxy-benzenesulfonyl)propyl, propyl group.

12. The process of claim 1 wherein $R_2$ is a substituted alkyl, aryl, or heteroaryl group having 1-30 carbon atoms.

13. The process of claim 12 wherein $R_2$ is a substituted alkyl selected from the group consisting of chloro-methyl, 1-bromopropyl, 1-bromopentyl, 1-bromo-2-methylpropyl, 1-bromo-tridecyl, nitromethyl, cyanomethyl, 4-nitrophenyl-methyl, 4-nitrophenylpropyl, 4-nitrophenoxymethyl, 1-(4-nitrophenoxy)propyl, 1-(4-nitrophenoxy)pentyl, 1-(4-nitrophenoxy)-2-methylpropyl, 1-(4-nitrophenoxy)-tridecyl, 1-(4-butylsulfonyl-aminophenoxy)tridecyl, 3-(4-nitrophenoxy)propyl, 2-phthalimidoethyl, 1-methyl-2-phthalimidoethyl, ethoxycarbonylmethyl, 1-dodecylsulfonylpropyl, 1-dodecyl-sulfonyl-2-methylpropyl, 1-tetradecylsulfonylpropyl, 1-hexadecylsulfonylpropyl, 1-(4-dodecyloxyphenylsulfonyl)propyl, 1-(4-hexadecyloxyphenylsulfonyl)propyl, and 2-octylsulfonylaminophenoxymethyl groups.

14. The process of claim 12 wherein $R_2$ is substituted aryl selected from the group consisting of 2-nitrophenyl, 3-nitrophenyl, 4-nitrophenyl, 4-chloro-3-nitrophenyl, 2-butoxy-5-nitrophenyl, 4-ethoxycarbonylphenyl, 3-do-decyloxyphenyl, 4-dodecyloxyphenyl, 4-tetradecyloxyphenyl, 4-hexadecyloxy-phenyl, and 2-(4-t-butylphenoxy)-5-nitrophenyl groups.

15. The process of claim 12 wherein $R_2$ is a substituted heteroaryl selected from the group consisting of 5-nitro-2-furyl, 2-butoxy-3-pyridyl, and 5-nitro-3-pyrazolyl groups.

16. The process of claim 1 wherein $R_1$ is a t-butyl group and $R_2$ is a 3-nitrophenyl group.

17. The process of claim 1 wherein $R_1$ is t-butyl group and $R_2$ is 4-nitrophenyl group.

18. The process of claim 1 wherein $R_1$ is t-butyl group and $R_2$ is 1-phthalimido-2-propyl group.

19. The process of claim 1 wherein $R_1$ is t-butyl group and $R_2$ is 4-nitrophenoxypropyl group.

* * * * *